(12) United States Patent
Knight et al.

(10) Patent No.: US 7,946,149 B1
(45) Date of Patent: May 24, 2011

(54) EXPLOSIVE PULSE TESTING OF PROTECTIVE SPECIMENS

(75) Inventors: David E. Knight, Vienna, VA (US);
William H. Lewis, Gaithersburg, MD (US); Philip John Dudt, Rockville, MD (US); Lemuel M. Bell, Waldorf, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1637 days.

(21) Appl. No.: 11/011,649

(22) Filed: Dec. 15, 2004

(51) Int. Cl.
*G01M 7/00* (2006.01)
(52) U.S. Cl. ...................................... 73/12.08; 73/35.14
(58) Field of Classification Search ........................ None
See application file for complete search history.

(56) References Cited

U.S. PATENT DOCUMENTS

| 4,479,378 A | * | 10/1984 | Malakhoff | 73/12.08 |
| 4,495,809 A | * | 1/1985 | Higginbotham et al. | 73/865.6 |
| 6,131,437 A | * | 10/2000 | Sanford | 73/12.09 |

* cited by examiner

*Primary Examiner* — Robert R Raevis
(74) *Attorney, Agent, or Firm* — Howard Kaiser

(57) ABSTRACT

A transducer is fixedly positioned within a supporting frame, covered by a shield in underlying relation to an enclosure within which explosion pulses are generated for testing purposes. The explosion pulses are profiled during emergence thereof through an aperture in the shield onto a specimen of cellular protective material to be tested by positioning thereof on the transducer. The enclosure is filled with a fluid media such as water to establish a water column corresponding for example to an underwater environment within which such explosion pulses would be generated. The energy of the profiled explosion pulses, not absorbed within the specimen, is measured through the transducer and recorded as a function of time for evaluation of the explosion protective capability of the specimen material being tested.

20 Claims, 2 Drawing Sheets

EXPLOSIVE PULSE TESTING OF PROTECTIVE SPECIMENS

STATEMENT OF GOVERNMENT INTEREST

The invention described herein may be manufactured and used by or for the Government of the United States of America for governmental purposes without the payment of any royalties thereon or therefor.

The present invention relates generally to the testing of specimens utilized for explosion protective or absorption purposes.

BACKGROUND OF THE INVENTION

Cellular materials have been utilized to resist being crushed during quasi-static and collision types of loading events. Compression or drop weight testing facilities have been used for load measurements of such cellular materials subject to loading during such events. However, no comparative method of testing of such cellular materials is presently available under extreme loading conditions associated with explosive detonations within air or underwater environments. It is therefore an important object of the present invention to provide for the testing of protective cellular materials, such as foamed plastics and honeycomb metal configurations, so as to provide data with respect to their capabilities and costs for absorbing explosive energy.

SUMMARY OF THE INVENTION

Pursuant to some embodiments of the present invention, a sample of the protective cellular material to be tested is prepared as a specimen positioned on top of a calibrated load transducer assembled between a frame supported base and a covering shield. An enclosure containing a water column is positioned on the shield. Explosion pulses generated within the water column enclosure are profiled by emergence through an aperture in the shield before being applied onto the specimen. Some embodiments of the present invention omit a water column, the cellular material specimen being tested by application of profiled air generated pulses. The energy is measured of the profiled explosion pulses transmitted without absorption through the specimen as a function of time. Equivalently expressed, the extent to which the energy of such profiled explosion pulses is absorbed by the specimen is measured by the calibrated load transducer as a function of time. The measurement can be recorded by a readout recorder electrically connected to the load transducer by a transmission cable.

BRIEF DESCRIPTION OF THE DRAWINGS

A more complete appreciation of the invention and many of its attendant advantages will be readily appreciated as the same becomes better understood by reference to the following detailed description when considered in connection with the accompanying drawing wherein.

DETAILED DESCRIPTION OF THE PREFERRED EMBODIMENT

Figure 1:
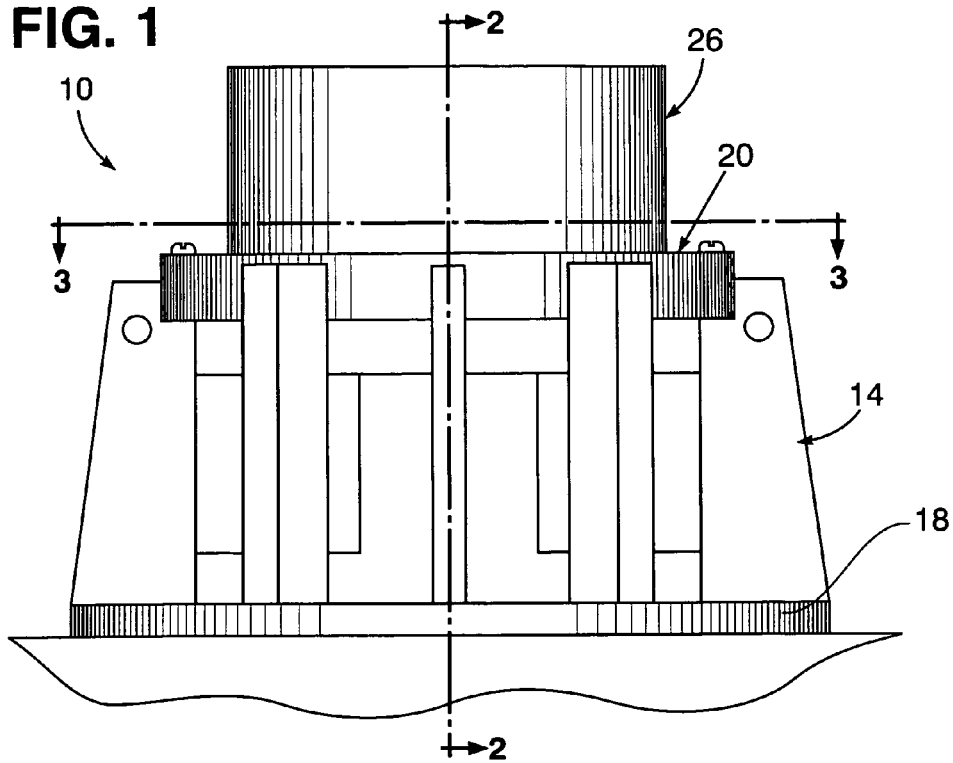
FIG. 1 is a side elevation view of a testing apparatus in accordance with one embodiment of the present invention.
Figure 2:
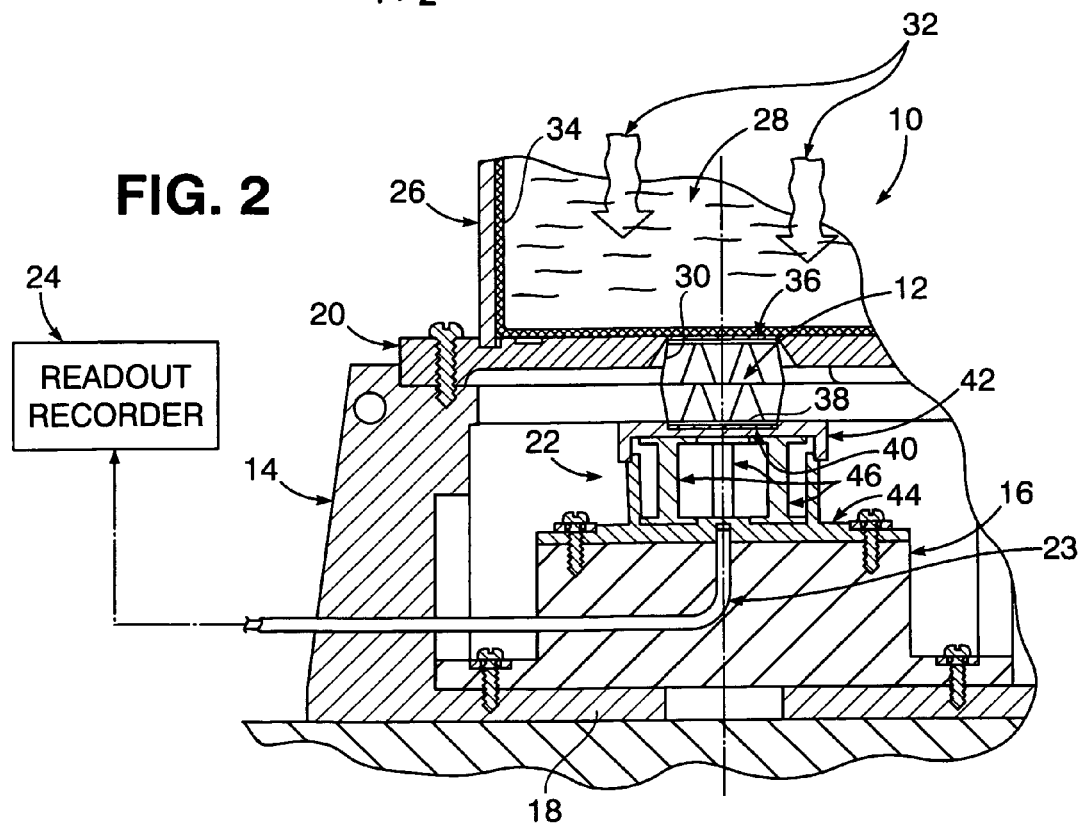
FIG. 2 is a partial section view taken substantially through a plane indicated by section line 2-2 in FIG. 1.
Figure 3:
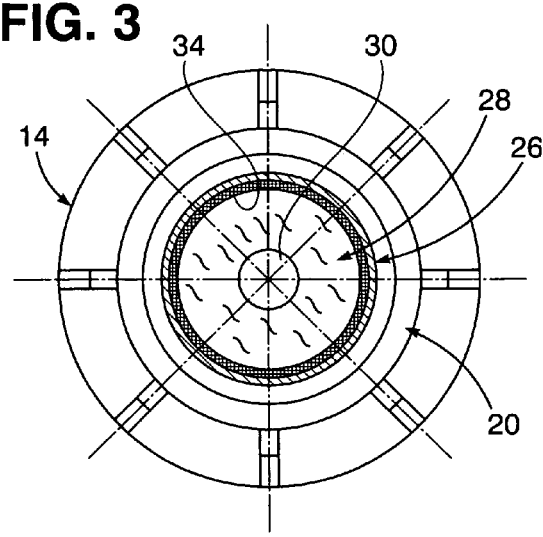
FIG. 3 is a transverse section view taken substantially through a plane indicated by section line 3-3 in FIG. 1.

Reference is now made to FIG. 1, FIG. 2 and FIG. 3, which illustrate an embodiment of an assembled testing apparatus 10 in accordance with the present invention. Cellular material specimen 12 is positioned therein as shown in FIG. 2. The inventive testing apparatus 10 features an outer support frame 14 within which a base 16 is fixedly positioned on a bottom support 18. The base 16 is spaced below a top cover shield 20 attached to the frame 14. The test specimen 12 is positioned on a load transducer 22 attached to the base 16 as shown in FIG. 2, from which a measurement transmission cable 23 extends out of the testing apparatus 10 to a diagrammatically illustrated measurement readout recorder 24. An explosion to be utilized for testing of the specimen 12 is performed at a fixed standoff distance above the specimen 12 within a compartment enclosure 26 enclosing a quantity of water such as a water column 28 positioned on top of the shield 20. A central opening aperture 30 is formed within the shield 20, through which the specimen 12 is subjected to the energy of profiled explosion pulses 32 as diagrammed in FIG. 2, generated by the testing explosion within the compartment enclosure 26. The enclosure 26 is shown internally lined with a (e.g., 4-6 mil.) waterproof membrane lining 34.

Figure 4:
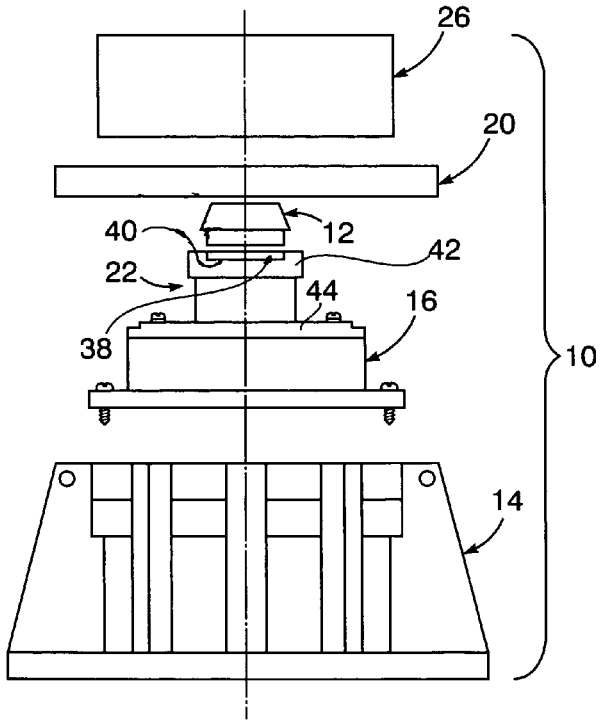
FIG. 4 is a side elevation view of disassembled components of the inventive testing apparatus shown in FIG. 1 and a test specimen positioned therein.

FIG. 4 shows the components of the testing apparatus 10, as hereinbefore described, disassembled with the specimen 12 shown positioned between the transducer 22 and the shield 20 located above the support frame 14 into which the transducer 22 is inserted and attached before sequential attachment of the shield 20 to the frame 14 and insertion of the water column enclosure 26 onto the shield 20. The specimen 12 is inserted onto the transducer 22 after such assembly of the apparatus 10 to initiate performance of a measurement method for testing of explosion pulse energy absorption by the specimen 12 as diagrammed in FIG. 5.

With reference to FIG. 2, the specimen 12 is positioned so as to project into a the aperture 30, formed within the shield 20, and contact an upper interface material layer 36 situated in the aperture 30. The bottom of the specimen 12 is then in contact with a lower interface material layer 38 positioned within a central recess 40 formed in a top tray portion 42 of the load transducer 22. The load transducer 22 has a bottom support portion 44 attached to the top of the base 16. The measurement signals are transmitted from the load transducer 22 through the cable 23. A plurality of parallel spaced vertical load gauge columns 46 of the load transducer 22 extend between and are attached to the support portion 44 and the tray portion 42. The load gauge columns 46 are calibrated to establish transducer measurement of the test explosive profiled pulse energy as a function of time.

Upon the occurrence of a test explosion, a quantity of explosive energy is encountered by specimen 12. Some of the explosive energy encountered by specimen 12 is absorbed by the specimen 12, and some of the explosive energy encountered by specimen 12 is not absorbed by the specimen 12. Load transducer 22 measures loading associated with the portion of explosive energy encountered by specimen 12 that is not absorbed by specimen 12 and that concomitantly is transmitted to load transducer 22. According to typical inventive practice, the amount of encountered explosive energy that is transmitted to load transducer 22 is commensurate with the amount of encountered explosive energy that is not absorbed by specimen 12. The higher is the measured loading, the higher is the energy unabsorbed by the specimen 12, and hence the lower is the energy absorbed by the specimen 12. The measurement by the load transducer 22 is thus indicative of the amount of encountered explosive energy that is not absorbed by the specimen 12 and that accordingly is transmitted by specimen 12 to load transducer 22. Furthermore, according to typical inventive practice, the load transducer 22 is calibrated with respect to a standard corresponding to complete non-absorption of encountered explosive energy by a specimen 12, the calibration standard thereby corresponding to complete transmission of encountered explosive energy to the load transducer 22; therefore, the measurement by load transducer 22 is not only indicative of the amount of encountered explosive energy that is not absorbed by specimen 12 (and is transmitted by specimen 12 to load transducer 22), but is also indicative of the amount of encountered explosive energy that is absorbed by specimen 12.

Figure 5:
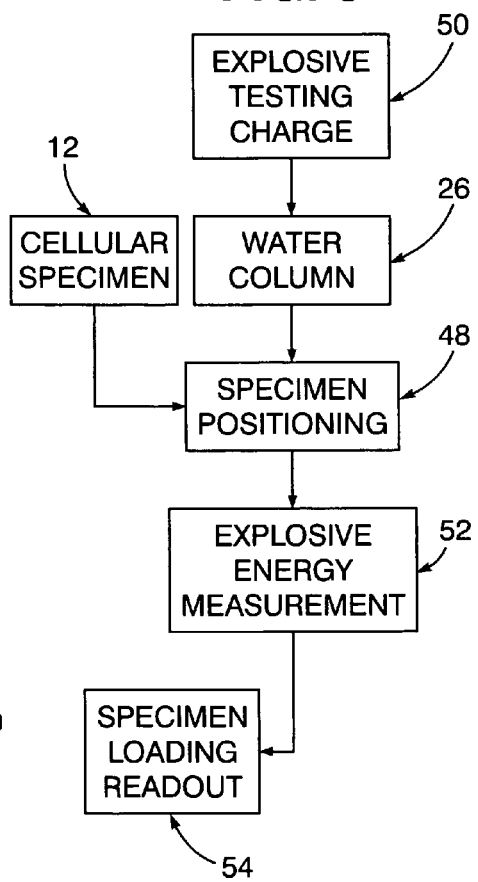
FIG. 5 is a diagram of an embodiment of an inventive testing method performed using the inventive testing apparatus illustrated in FIGS. 1-4.

Based on the foregoing description of the inventive testing apparatus 10, an embodiment of an inventive measurement method is performed as diagrammed in FIG. 5. Initially the specimen 12 undergoes a positioning step 48 for placement within the assembled testing apparatus 10 between the water column enclosure 26 and the load transducer 22, before the step 50 of applying an explosive testing charge followed by a measurement step 52. Finally, a specimen loading readout step 54 is obtained from the load transducer 22 to determine energy absorption by the specimen 12 at extreme loading rates associated with the pulses 32 explosively generated within the enclosure 26.

Alternatively, the explosive pulses may be generated within air corresponding to an air environment, as distinguished from being generated within water (such as water 28 contained in enclosure 26) corresponding to an underwater environment. Specimens such as the specimen 12 may be quickly tested with quick turnarounds, and a permanent record may be provided with regard to each specimen by the readout recorder 24, in this manner determining explosive pulse loading as a function of time with regard to each of plural specimens for comparative purposes.

Obviously, other modifications and variations of the present invention may be possible in light of the foregoing teachings. It is therefore to be understood that within the scope of the appended claims the invention may be practiced otherwise than as specifically described.

What is claimed is:

1. An apparatus for testing absorbency of an object with respect to energy associated with an explosion, the apparatus comprising:
    a shield characterized by an aperture having a horizontal periphery;
    a load transducer including an upper transducer structure and a lower transducer structure, said upper transducer structure being characterized by a recess having a horizontal recessed surface;
    a base on which said lower transducer structure is mounted;
    a housing securing said shield and said base;
    an upper interface member that is conformal with said aperture; and
    a lower interface member that is conformal with said recess;
    said apparatus being combinable with a specimen so that:
        said specimen is sandwiched between said upper interface member and said lower interface member; said upper interface member is in a horizontal position in said aperture; said lower interface member is in a horizontal position in said recess and adjoining said recessed surface; upon detonation of an explosive device that is distanced above said upper interface member, a quantity of explosive energy is encountered by said specimen so that a first portion of the encountered explosive energy is absorbed by said specimen and a second portion of the encountered explosive energy is not absorbed by said specimen and is transmitted to said load transducer; said load transducer measures loading associated with said second portion of the encountered explosive energy; said loading measurement by said load transducer is indicative of the amount of said second portion of the encountered explosive energy.

2. The apparatus for testing absorbency as defined in claim 1, wherein:
    said load transducer is calibrated with respect to a standard corresponding to approximately zero amount of said first portion of the encountered explosive energy and corresponding to approximately complete transmission of the encountered explosive energy to said load transducer;
    based on said calibration of said load transducer, said loading measurement by said load transducer is indicative of the amount of said first portion of explosive energy.

3. The apparatus for testing absorbency as defined in claim 2, the apparatus further comprising a recorder connected to said load transducer, said recorder being for recording said loading measurement by said load transducer as a function of time.

4. The apparatus for testing absorbency as defined in claim 1, said load transducer further including plural vertical loading gauge columns that respond to said loading associated with said second portion of explosive energy, said structures adjoining said loading gauge columns at opposite ends of said loading gauge columns.

5. The apparatus for testing absorbency as defined in claim 4, the apparatus further comprising a recorder connected to said load transducer, said recorder being for recording said loading measurement by said load transducer as a function of time.

6. The apparatus for testing absorbency as defined in claim 4, wherein said load transducer is calibrated so that said measurement by said load transducer is indicative of the amount of said first portion of the encountered explosive energy.

7. The apparatus for testing absorbency as defined in claim 6, the apparatus further comprising a recorder connected to said load transducer, said recorder being for recording said loading measurement by said load transducer as a function of time.

8. The apparatus for testing absorbency as defined in claim 1, the apparatus further comprising a recorder connected to said load transducer, said recorder being for recording said loading measurement by said load transducer as a function of time.

9. The apparatus for testing absorbency as defined in claim 1, the apparatus further comprising an enclosure including a waterproof membrane for containing a body of water, said enclosure being placed on said shield so that said membrane is situated adjacent to said upper interface member and so that said body of water is situated proximate said upper interface member, wherein said explosive device when detonated is submerged in said body of water contained by said membrane.

10. The apparatus for testing absorbency as defined in claim 9, wherein said load transducer is calibrated so that said loading measurement by said load transducer is indicative of the amount of said first portion of the encountered explosive energy.

11. The apparatus for testing absorbency as defined in claim 10, the apparatus further comprising a recorder connected to said load transducer, said recorder being for recording said loading measurement by said load transducer as a function of time.

12. The apparatus for testing absorbency as defined in claim 9, said load transducer further including plural vertical loading gauge columns that respond to said loading associated with said second portion of the encountered explosive energy, said structures adjoining said loading gauge columns at opposite ends of said loading gauge columns.

13. The apparatus for testing absorbency as defined in claim 12, the apparatus further comprising a recorder connected to said load transducer, said recorder being for recording said loading measurement by said load transducer as a function of time.

14. The apparatus for testing absorbency as defined in claim 12, wherein said load transducer is calibrated so that said loading measurement by said load transducer is indicative of the amount of said first portion of encountered explosive energy.

15. The apparatus for testing absorbency as defined in claim 14, the apparatus further comprising a recorder connected to said load transducer, said recorder being for recording said loading measurement by said load transducer as a function of time.

16. The apparatus for testing absorbency as defined in claim 9, the apparatus further comprising a recorder connected to said load transducer, said recorder being for recording said loading measurement by said load transducer as a function of time.

17. A method for testing absorbency of an object with respect to energy associated with an explosion, the method comprising:

provpiding an apparatus that includes a shield, a load transducer, a base, a housing, an upper interface member, and a lower interface member, said shield being characterized by an aperture having a horizontal periphery, said load transducer including an upper transducer structure and a lower transducer structure, said upper transducer structure being characterized by a recess having a horizontal recessed surface, said lower transducer structure being mounted on said base, said housing securing said shield and said base, said upper interface member being conformal with said aperture, said lower interface member being conformal with said recess;

positioning a specimen between said upper interface member and said lower interface member so that said upper interface member is in a horizontal position in said aperture and so that said lower interface member is in a horizontal position in said recess and adjoining said recessed surface;

detonating an explosive device that is distanced above said upper interface member; and measuring loading associated with a second portion of explosive energy, said measuring including using said load transducer, wherein a first portion of explosive energy is absorbed by said specimen and said second portion of explosive energy is not absorbed by said specimen and is transmitted to said load transducer, and wherein said measured loading is indicative of the amount of said second portion of explosive energy.

18. The method for testing absorbency as defined in claim 17, wherein the method further comprises recording said measured loading as a function of time.

19. The method for testing absorbency as defined in claim 17, wherein:

said load transducer is calibrated;

based on said calibration of said load transducer, said measurement by said load transducer is indicative of the amount of said first portion of explosive energy.

20. The method for testing absorbency as defined in claim 17, wherein:

said apparatus further includes an enclosure that includes a waterproof membrane for containing a body of water;

said method further comprises placing said enclosure on said shield so that said membrane is situated adjacent to said upper interface member and so that said body of water is situated proximate said upper interface member; and said detonating of said explosive device is performed while said explosive device is submerged in said body of water contained by said membrane.

\* \* \* \* \*